United States Patent [19]

Shah

[11] Patent Number: 4,713,237
[45] Date of Patent: Dec. 15, 1987

[54] SUSTAINED RELEASE DOSAGE FORM

[75] Inventor: Mahendra Shah, Lake Hiawatha, N.J.

[73] Assignee: Schering Corporation, Kenilworth, N.J.

[21] Appl. No.: 621,580

[22] Filed: Jun. 18, 1984

[51] Int. Cl.[4] .......................... A61K 9/22; A61K 9/52; A61K 31/74; A61K 31/78

[52] U.S. Cl. ......................................... 424/78; 424/81; 424/452; 424/457; 424/464; 424/465; 424/468; 424/484; 424/487; 424/489

[58] Field of Search ....................... 424/19, 78, 31, 81, 424/452, 457, 464, 465, 468, 484, 487, 489; 525/54.32

[56] References Cited

U.S. PATENT DOCUMENTS

| | | |
|---|---|---|
| 3,495,000 | 2/1970 | Merabi et al. ................... 424/22 |
| 3,577,512 | 6/1986 | Shepherd et al. ................ 424/21 |
| 3,661,815 | 5/1972 | Smith ............................ 525/54.32 |
| 3,909,444 | 9/1975 | Anderson et al. .............. 252/316 |
| 3,919,436 | 11/1975 | Tukobe et al. ................... 424/33 |
| 4,116,899 | 9/1978 | Fanta ........................... 260/17.4 GC |
| 4,159,260 | 6/1979 | Jones et al. ................... 260/17.4 GC |
| 4,265,875 | 5/1981 | Byrne et al. ..................... 424/19 |
| 4,304,591 | 12/1981 | Mueller et al. .................. 424/19 |

OTHER PUBLICATIONS

Das. Controlled Release Technology, Bioengineering Aspects, John Wiley & Sons.

Primary Examiner—Shep K. Rose
Attorney, Agent, or Firm—Richard C. Billups; James R. Nelson; Stephen I. Miller

[57] ABSTRACT

Sustained release dosage forms are made of saponified starch-acrylonitrile graft copolymers and an active ingredient.

3 Claims, No Drawings

SUSTAINED RELEASE DOSAGE FORM

This invention relates to dosage forms capable it slowly releasing active ingredients.

Numerous prior publications disclose various polymers for slowly releasing active ingredients. See for example Schor et al, U.S. Pat. No. 4,369,172 (hydroxypropylmethyl cellulose); Hasler et al, U.S. Pat. No. 4,105,823 (starches, polyanhydrides, polyacrylamide and acrylates); Dannelly, U.S. Pat. No. 4,177,255 (cellulose esters, polyvinylchloride polystyrene, polymethyl methacrylate, etc); Shepherd et al, U.S. Pat. No. 3,577,512 (hydrophilic acrylates); Takeabe et al, U.S. Pat. No. 3,919,436 (substituted acrylamide); Merabi et al, U.S. Pat. No. 3,495,000 (dialdehyde starch mixed with other ingriedients); and Anderson et al, U.S. Pat. No. 3,909,444 (various synthetic polymers and cellulose derivative).

The present invention concerns use of saponified starch-acrylonitrile graft copolymers for sustained release of active ingredients. It is believed that this particular copolymer has not previously been used for this purpose. These graft copolymers are known to be water swellable, but not water soluble. Surprisingly it has been found that saponified starch-acrylonitrile graft copolymers provide highly desirable sustained release of the active ingredient.

SUMMARY OF THE INVENTION

The present invention comprises a sustained release dosage form conprising an active ingredient and saponified starch-acrylonitrile graft copolymer.

DETAILED DESCRIPTION OF THE INVENTION

Saponified starch-acrylonitrile graft copolymers are manufactured by preparing a graft copolymer of starch and acrylonitrile with starch as the backbone and acrylonitrile as the branches. The copolymer is then saponified in a solution of alkali metal hydroxide to form a copolymer having a structure equivalent to a starch-acrylamide-akali metal acrylate graft copolymer wherein starch is the backbone and acrylamide and alkali metal acrylate form the branches. This manufacturing process is described in U.S. Pat. Nos. 3,661,815, 4,116,899, and a product brochure entitled SGP ABSORBENT POLYMER published by Henkel Corporation, incorporated by reference. The graft copolymer may be blended with fatty quaternary ammonium chloride as described in U.S. Pat. No. 4,159,260, incorporated by reference.

More particularly, as stated in the Henkel brochure, the structure of the absorbent polymer is as follows:

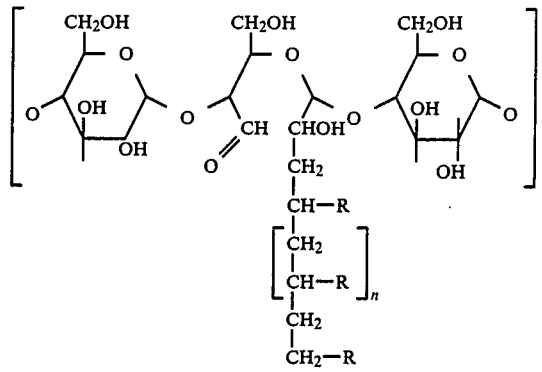

where $R = -CONH_2$ or $-CO_2Na$.

Suitable saponified starch-acrylonitrile graft copolymers are sold under the tradenames SGP by Henkel Corporation, Minneapolis, MN. and WATERLOCK by Grain Processing Corporation, Muscatine, Iowa. These products are known for their ability to absorb large quantities of water, but their use in slow release dosage forms is belived novel.

To make sustained release dosage forms in accordance with the invention, the saponified starch-acrylonitrile graft copolymers are blended with the active ingredient and then formed into the desired dosage form by methods well known to those skilled in the art. Examples of dosage forms include capsules, oral liquids, tablets, implants, topical lotions, creams or ointments, opthalmic gels, vaccines, injectable solutions and suspensions, suppositories, etc. Active ingredients may be any desirable substance or combination of substances such as aspirin, salicylic acid, sodium salicylate, APAP, steroids, antibiotics, pilocarpine, pseudophedrine base, pseudophedrine sulfate, chloramphenicol, antibiotics, polypeptides, growth promoter, anthelmintics, etc.

To make sustained dosage forms in accordance with the invention, saponified starch-acrylonitrile graft copolymer is mixed with the active ingredient and the mixture is then placed into the desired form. For example, to form a tablet, compress the mixture in a conventional tablet press. To form a suspension for injection or oral administration, mix the mixture with appropriate liquids.

EXAMPLES

The following examples illustrate the effect of saponified starch-acrylonitrile graft copolymer on the slow release of various active ingredients. Two graft copolymers were used: (1) SGP 502S, manufactured by Henkel Corporation, and (2) SGP 104, which is made by blending SGP 502S with a fatty quaternary ammonium chloride.

For all examples, tablets were made by compressing 250 mg of a mixture of active ingredient and graft copolymer at 4000 lb pressure on a Carver Tablet press using 11/36" standard concave punches.

To test the release properties of the tablet, simulated gastric fluid (SGF) and simulated intestinal fluid (SIF) were prepared according to USP XX. The dissolution rates of the active ingredients were determined at various times at 37° C.

EXAMPLES WITH SALICYLIC ACID AS THE ACTIVE INGREDIENT

| | | Example No. | | |
|---|---|---|---|---|
| | 1 | 2 | 3 | 4 |
| Wt. % SGP 104 | 0 | 30 | 50 | 70 |
| Wt. % Salicylic Acid | 100 | 70 | 50 | 30 |
| Time, Hrs | Fluid | % Salicylic Acid Dissolved | | |
| 1 | SGF | 13 | 48 | 12 | 14 |
| 2 | SIF | 45 | 87 | 21 | 30 |
| 3 | SIF | 68 | | 32 | 49 |
| 4 | SIF | 83 | | 44 | 69 |
| 5 | SIF | 97 | | 57 | 82 |
| 6 | SIF | | | 65 | 90 |
| 18 | SIF | | | 103 | 101 |

The above examples show how the dissolution rate of salicylic acid can be varied with varying concentrations of the graft copolymer.

| | | Example No. | | |
|---|---|---|---|---|
| | 5 | 6 | 7 | 8 |
| Wt. % SGP 502S | 0 | 30 | 50 | 70 |
| Wt. % Salicylic Acid | 100 | 70 | 50 | 30 |
| Time, Hrs | Fluid | % Salicylic Acid Dissolved | | |
| 1 | SGF | 13 | 8 | 10 | 18 |
| 2 | SIF | 45 | 18 | 23 | 39 |
| 3 | SIF | 68 | 28 | 40 | 65 |
| 4 | SIF | 83 | 37 | 56 | 80 |
| 5 | SIF | 97 | 43 | 65 | 103 |
| 6 | SIF | | 49 | 72 | |
| 24 | SIF | | 102 | 100 | |

EXAMPLES WITH SODIUM SALICYLATE AS THE ACTIVE INGREDIENT

| | | Example No. | | |
|---|---|---|---|---|
| | 9 | 10 | 11 | 12 |
| Wt. % SGP 104 | 0 | 30 | 50 | 70 |
| Wt. % Sodium Salicylate | 100 | 70 | 50 | 30 |
| Time, Hrs | Fluid | % Sodium Salicylate Dissolved | | |
| 1 | SGF | 100 | 102 | 28 | 24 |
| 2 | SIF | | | 57 | 47 |
| 3 | SIF | | | 77 | 67 |
| 4 | SIF | | | 84 | 78 |
| 5 | SIF | | | 89 | 86 |

| | | Example No. | | |
|---|---|---|---|---|
| | 13 | 14 | 15 | 16 |
| Wt. % SGP 502S | 0 | 30 | 50 | 70 |
| Wt. % Sodium Salicylate | 100 | 70 | 50 | 30 |
| Time, Hrs | Fluid | % Sodium Salicylate Dissolved | | |
| 1 | SGF | 100 | 102 | 32 | 28 |
| 2 | SIF | | | 71 | 63 |
| 3 | SIF | | | 84 | 79 |
| 4 | SIF | | | 92 | 89 |
| 5 | SIF | | | 95 | 94 |

Examples 9 through 16 show how a very rapidly dissolving active ingredient can be slowly released using the present invention.

EXAMPLES WITH PSEUDOEPHEDRINE BASE (PB) AS THE ACTIVE INGREDIENT

| | | Example No. | | | |
|---|---|---|---|---|---|
| | 17 | 18 | 19 | 20 | 21 |
| Wt. % SGP 104 | 0 | 30 | 50 | 60 | 70 |
| Wt. % PB | 100 | 70 | 50 | 40 | 30 |
| Time, Hrs | Fluid | % PB Dissolved | | | |
| 1 | SGF | 100 | 63 | 25 | 21 | 24 |
| 2 | SIF | | 100 | 62 | 30 | 32 |
| 3 | SIF | | | 87 | 45 | 43 |
| 4 | SIF | | | 95 | 57 | 64 |
| 5 | SIF | | | | 70 | 78 |
| 6 | SIF | | | | 83 | 93 |
| 7 | SIF | | | | 89 | |

| | | Example No. | | | |
|---|---|---|---|---|---|
| | 22 | 23 | 24 | 25 | 26 |
| Wt. % SGP 502S | 0 | 30 | 50 | 60 | 70 |
| Wt. % PB | 100 | 70 | 50 | 40 | 30 |
| Time, Hrs | Fluid | % PB Dissolved | | | |
| 1 | SGF | 100 | 64 | 25 | 21 | 22 |
| 2 | SIF | | 95 | 66 | 30 | 28 |
| 3 | SIF | | | 90 | 45 | 34 |
| 4 | SIF | | | 96 | 57 | 40 |
| 5 | SIF | | | | 70 | 58 |
| 6 | SIF | | | | 83 | 59 |
| 7 | SIF | | | | 89 | |

Example 17 to 26 also illustrate the sustained release of a rapidly dissolving ingredient.

EXAMPLES WITH PSEUDOEPHEDRINE SULFATE (PS) AS THE ACTIVE INGREDIENT

| | | Example No. | | | |
|---|---|---|---|---|---|
| | 27 | 28 | 29 | 30 | 31 |
| Wt. % SGP 104 | 0 | 30 | 40 | 50 | 70 |
| Wt. % PS | 100 | 70 | 60 | 50 | 30 |
| Time, Hrs | Fluid | % PS Dissolved | | | |
| 1 | SGF | 100 | 94 | 45 | 39 | 33 |
| 2 | SIF | | | 63 | 52 | 40 |
| 3 | SIF | | | 69 | 59 | 45 |
| 4 | SIF | | | 79 | 66 | 52 |
| 5 | SIF | | | 82 | 69 | 58 |
| 6 | SIF | | | 87 | 76 | 65 |
| 7 | SIF | | | 89 | | |

| | | Example No. | | | |
|---|---|---|---|---|---|
| | 32 | 33 | 34 | 35 | 36 |
| Wt. % SGP 502S | 0 | 30 | 40 | 50 | 70 |
| Wt. % PS | 100 | 70 | 60 | 50 | 30 |
| Time, Hrs | Fluid | % PS Dissolved | | | |
| 1 | SGF | 100 | 56 | 30 | 24 | 25 |
| 2 | SIF | | 76 | 41 | 33 | 32 |
| 3 | SIF | | 87 | 47 | 38 | 38 |
| 4 | SIF | | | 52 | 44 | 45 |
| 5 | SIF | | | 59 | 48 | 46 |
| 6 | SIF | | | 62 | 52 | 51 |
| 7 | SIF | | | 67 | 57 | 55 |

EXAMPLES WITH CHLORAMPHENICOL (C) AS THE ACTIVE INGREDIENT

| | | Example No. | | |
|---|---|---|---|---|
| | 37 | 38 | 39 | 40 |
| Wt. % SGP 104 | 0 | 30 | 50 | 70 |
| Wt. % C | 100 | 70 | 50 | 30 |
| Time, Hrs | Fluid | % C Dissolved | | |
| 1 | SGF | 5 | 67 | 37 | 14 |
| 2 | SIF | 26 | 92 | 87 | 50 |
| 3 | SIF | 42 | | | 61 |
| 4 | SIF | 53 | | | 93 |

-continued

| | | | | |
|---|---|---|---|---|
| 5 | SIF | 62 | | 104 |
| 6 | SIF | 70 | | |
| 7 | SIF | 75 | | |

In Examples 38 to 40, the graft copolymers increased the rate of dissolution of the active ingredient, which could be advantageous in many cases.

| | | Example No. | | | | |
|---|---|---|---|---|---|---|
| | | 41 | 42 | 43 | 44 | 45 |
| Wt. % SGP 502S | | 0 | 30 | 50 | 60 | 70 |
| Wt. % C | | 100 | 70 | 50 | 40 | 30 |
| Time, Hrs | Fluid | % C Dissolved | | | | |
| 1 | SGF | 5 | 85 | 12 | 13 | 9 |
| 2 | SIF | 26 | 91 | 77 | 51 | 14 |
| 3 | SIF | 42 | | 86 | 74 | 19 |
| 4 | SIF | 53 | | 95 | 91 | 24 |

-continued

| | | | | |
|---|---|---|---|---|
| 5 | SIF | 62 | 97 | 30 |
| 6 | SIF | 70 | 100 | 35 |
| 7 | SIF | 75 | | — |
| 24 | SIF | | | 103 |

It can be seen the tablets provide highly desirable release patterns for active ingriedients.

What is claimed is:

1. A sustained release dosage form comprising an effective amount of active ingredient and an effective amount of a water insoluble, water swellable, saponified starch acrylonitrile graft copolymer to provide sustained release of said active upon oral administration to a patient in need of such treatment.

2. A sustained release dosage form according to claim 1 wherein the dosage form further comprises a capsule for oral administration.

3. A sustained release dosage form according to claim 1 wherein the dosage form further comprises a tablet for oral administration.

* * * * *